United States Patent [19]

Hayes

[11] Patent Number: 6,123,918
[45] Date of Patent: Sep. 26, 2000

[54] *HYPEROLIUS ARGUS* ENDOCRINE SCREEN TEST

[75] Inventor: Tyrone B. Hayes, Berkeley, Calif.

[73] Assignee: The Regents of the University of California, Oakland, Calif.

[21] Appl. No.: 09/044,221

[22] Filed: Mar. 18, 1998

[51] Int. Cl.[7] .......................... A61K 49/00; G01N 31/00; G01N 33/48

[52] U.S. Cl. .......................... 424/9.2; 424/520; 424/562; 424/568; 424/9.1

[58] Field of Search ...................................... 424/1.11, 520, 424/562, 568, 9.2, 9.1; 206/223, 569, 570; 530/399; 540/2; 435/6; 552/502; 119/6.5

[56] References Cited

PUBLICATIONS

Hayes, T.B., 1997, "Hormonal Mechanisms as Potential Constraints on Evolution: Examples form the Anura," *Amer. Zoo.* 37:482–490.

Richards, C.M., 1982, "The Alteration of Chromatophore Expression by Sex Hormones in the Kenyan Reed Frog, *Hyperolius viridiflavus*," *Gen. Comp. Endocrin.* 46:59–67.

Blair, A.P., 1946, "Effects of Various Hormones on Primary and Secondary Sex Characters of Juvenile *Bufo fowleri*," *J. Exp. Zool.* 103:365–400.

Greenberg, B., 1942, Some Effects of Testosterone on the Sexual Pigmentation and Other Sex Characters of the Cricket Frog (*Acris gryllus*), *J. Exp. Zool.* 91:435–451.

*Primary Examiner*—Jose' G. Dees
*Assistant Examiner*—Dameron Jones
*Attorney, Agent, or Firm*—Klarquist Sparkman Campbell Leigh & Whinston, LLP

[57] ABSTRACT

Compounds and samples may be screened for estrogenic, androgenic, and thyroid hormone activity simultaneously, by administering the compound or sample to larval amphibians or tissue obtained therefrom, particularly *Hyperolius argus*, prior to the end of metamorphosis, and observing developmental differences between the test amphibians and normal development for said amphibians.

24 Claims, No Drawings

*HYPEROLIUS ARGUS* ENDOCRINE SCREEN TEST

STATEMENT AS TO FEDERALLY SPONSORED RESEARCH

This invention resulted from research funded in whole or part by the National Science Foundation, Grant No. IBN-9513362. The Federal Government may have certain rights in this patent.

BACKGROUND OF THE INVENTION

Screening tests are now used commonly to test compounds for potential pharmaceutical activity, and to test the environment for the presence of possibly deleterious substances. Some compounds are easily detected using standard chemical and spectroscopic techniques, while others are determined by their quick inflammatory or toxic effects on a test organism. However, there are many compounds (both potential pharmaceutical compounds and potential pollutants) that affect organisms developmentally. Developmental effects are more difficult and time-consuming to detect, as screens for such may require that one observe a test subject over the course of the organisms entire development. Bacteria, yeast, and isolated cell cultures may be poor test organisms, for failure to react and develop in a way analogous to higher animals.

SUMMARY OF THE INVENTION

A new developmental assay has been invented, which is sensitive, predictive, relatively rapid, and easy to execute. The assay simultaneously indicates the presence of compounds agonistic and/or antagonistic to estrogen, androgens, and thyroid hormone, by following the reaction of certain reed frog larvae or isolated skin to the presence of test compounds in their culture media.

One aspect of the invention is an assay for detecting hormonal activity in a sample by providing a hormone-responsive tissue from the larva of a hormone-responsive amphibian species, contacting the tissue with a sample, and observing the presence of absence of indicia characteristic of hormonal activity of the amphibian species.

Another aspect of the invention is a kit for detecting hormonal activity in a sample, comprising hormone-responsive tissue from the larva of a hormone-responsive amphibian species, and one or more positive controls selected from the group consisting of estrogenic, androgenic, and thyroid hormone agonists and/or antagonists.

The invention advantageously provides a method for determining estrogenic, androgenic, and/or thyroid hormone activity in a sample simultaneously. The invention further provides a convenient and simple bioassay for such activities.

DETAILED DESCRIPTION OF THE INVENTION

Definitions:

The terms "larva", "larval individual", and "larvae" all refer to immature, pre-metamorphosis forms of the selected amphibian species. Where the selected species is a frog, the larvae are commonly known as tadpoles.

The term "hormonal activity" as used herein refers to the ability of a compound to cause differences in development and/or maturation normally associated with hormones such as estrogen, testosterone, thyroid hormone, and the like, or to prevent or alter normal hormone-derived development. For example, the pesticide DDT exhibits estrogenic hormonal activity, and causes male frogs to develop spotting characteristic of female frogs in the assay of the invention. Hormonal activity may be either agonistic or antagonistic, for example, samples may be assayed for their ability to prevent estradiol-induced spot development in male frogs.

The term "hormone-responsive amphibian species" refers to a species of amphibian which responds to the presence of a compound with hormonal activity during metamorphosis with indicia characteristic of the animal's reaction to the hormone in question. Hormone-responsive amphibian species react to mammalian steroid hormones, thyroid hormone, and the like, with great sensitivity. For example, *Hyperolius argus* reacts to the presence of 100 pg/ml estradiol during metamorphosis, resulting in male frogs having spotting characteristic of female *Hyperolius argus*. The indicia resulting from contacting a hormone-responsive amphibian species with a compound with hormonal activity is generally an easily observed developmental feature. Sexually dimorphic species are particularly useful, as the differences between the sexes can be easily observed, and used to indicate the response to an estrogenic or androgenic compound.

General Method and Description:

A suitable hormone-responsive amphibious species is first selected. The species should be selected for easily discernable differences between responses to estrogenic and androgenic hormones. Species with a large degree of sexual dimorphism are preferred for this reason. The species should exhibit clearly different responses to estrogens and androgens (for example, if individuals of the species react to estrogens by changing skin color, they should not change to the same color in response to androgens). The species should undergo metamorphosis at a well-defined time, with characteristic end points, and should be consistent from individual to individual within the species. Preferably, the species selected will be very sensitive to estrogenic compounds and androgenic compounds, and will mature rapidly. Ideally, the species should also breed rapidly, breed well in captivity, require little space for housing, and have few or no expensive requirements for keeping and breeding.

The *Hyperolius argus*, a small Reed Frog indigenous to northeastern Africa, is sexually dimorphic at maturity. At metamorphosis, both males and females are colored bright green on the dorsal surface. At sexual maturity, the males develop a gular (vocal) pouch, while the females develop dark spots, changing to white over a few days, after which the background color changes from green to red, and the toes turn yellow. These color changes are not observed in the males, while the gular pouch is not observed in females.

The assay of the invention is conducted by exposing frog larvae such as *Hyperolius argus*, to the compounds to be tested prior to metamorphosis, and observing the developmental changes that occur, and their differences from normal frog development. The test compounds are typically diluted serially over a range of concentrations, and are added to the culture medium containing the frog larvae at some point prior to metamorphosis. Larvae cultures may contain one or more larvae. The assay may begin with larvae shortly after hatching, or may begin as late as about six days prior to the end of metamorphosis. Typically, standard positive and negative controls are also performed, using for example 17 β estradiol as a positive control for estrogenic compounds, testosterone or dihydrotestosterone as a positive control for androgenic compounds, and thiourea as a thyroid hormone antagonist control. Compounds that exhibit estrogenic activity cause the frogs to develop the spots characteristic of females. Compounds that exhibit androgenic activity cause the frogs to develop gular pouches characteristic of males. Addition of estrogenic and/or androgenic compounds during metamorphosis causes the corresponding changes to occur immediately, rather than at sexual maturity (which is typically several months after completion of metamorphosis). Compounds that antagonize thyroid hormone reduce or prevent tail resorption. In each case, compounds with greater activity are found to cause the corresponding changes at a faster rate, for example, a weakly estrogenic compound might cause spotting over an eight-day period, while a strongly estrogenic compound might cause spotting over a four-day period. The pathways involved are essentially independent, which renders the assay capable of detecting estrogenic, androgenic, and thyroid hormone activity simultaneously in the same assay. This renders the assay particularly useful for detecting pollutants having hormone-like activity, and for screening biological extracts and combinatorial libraries for possible pharmaceutical activities.

To screen compounds for potential pharmaceutical activity, a sample containing the compounds is typically dissolved in water or other suitable carrier in a range of concentrations, and added to the water containing the test larvae. If the addition fluid requires a non-aqueous solvent (e.g., toluene, acetonitrile, ethanol, and the like), "blank" samples (samples containing only the non-aqueous solvent) should also be included as controls. The assay of the invention permits one to assay one or more compounds simultaneously for several potential activities (for example, estrogenic, androgenic, and thyroid hormone activities). Samples may contain, for example without limitation, individual compounds, supernatants or culture broths, or mixtures or pools of compounds, with the identity of compounds responsible for activity determined by iteration with subsets of positive pools. To screen environmental samples for possible pollutants, a similar procedure is followed. Samples may consist of, for example, ground water, lake or pond water, effluent, suspended soil samples, and the like.

Alternatively, these assays may be performed with isolated dorsal skin (for estrogenic assays), ventral skin (for androgenic assays), and/or tails (for thyroid hormone assays). These in vitro assays are advantageous in that the skin and tail from one animal may be exposed to a number of different compounds individually (by dividing the skin and tail into portions), and that the skin hormonal responses may be isolated from any other hormonal response that the intact frog might otherwise generate. To perform the assays in vitro, dorsal and/or ventral skin, and/or tail tips are isolated from *Hyperolius argus* larvae about 6–7 days prior to metamorphic climax, and are allowed to recover in culture medium for about 24 hours. The skin and/or tail samples may be divided into multiple pieces, to conduct multiple assays. The samples are then treated with the test compounds as set forth above for intact animals.

*Hyperolius argus* are presently preferred test organisms. They are small (adults approximately 2.5 cm), reach maturity in only four months (in contrast to the 2–3 years required for *Xenopus laevis* and many other amphibians), and produce eggs (after maturity) ever 2–3 weeks. Ten breeding pairs may be housed in a 5"×11"×6" space, and can produce up to about 4,000 eggs per month.

EXAMPLES

The following examples are provided as a guide to those of ordinary skill in the art, and are not to be considered as limiting the claims in any way. All experiments are conducted under ambient conditions of temperature, pressure, and the like, unless noted otherwise.

Example 1

Estrogenic Compounds (A) Compound discrimination: *Hyperolius argus* larvae were treated with a variety of different steroids at the metamorphic climax (start of tail resorption). Each compound was administered only once, at the beginning of treatment, at 100 ng/ml (except for 17-$SO_4$ E2, which produced effects only at concentrations $\geq 1$ μg/ml), and the animal observed for the next seven days (until tail resorption was complete). Each compound was tested on at least five animals. The results are set forth in Table 1.

TABLE 1 treatment of male *Hyperolius argus* with estrogenic compounds.

| Compound (100 ng/ml) | Spotting |
|---|---|
| Control | − |
| 17β E2 | ++ |
| 17α E2 | ++ |
| Estrone | ++ |
| Estriol | ++ |
| Estetrol | ++ |
| 2-OH E2 | ++ |
| 4-OH E2 | ++ |
| 11-OH E2 | ++ |
| 3-MeOH E2 | + |
| 2,3-diOH E2 | − |
| 3-gluc E2 | + |
| 17-gluc E2 | ++ |
| 17-$SO_4$ E2 (1 μg/ml) | + |
| 3,15-di$SO_4$ E2 | − |
| 3-$SO_4$, 17-gluc E2 | ++ |
| 17-benzoate E2 | ++ |
| 17-ethynyl E2 | ++ |
| 17-propionate E2 | ++ |
| cortisol | − |
| corticosterone | − |
| aldosterone | − |
| androstenedione | − |
| testosterone | − |
| dihydrotestosterone | − |

(E2 = estradiol, gluc = glucose, MeO = methoxy)

As shown in Table 1, only compounds having estrogenic activity demonstrated estrogenic results, corresponding in effect to the activity of the compound. Non-estrogenic steroids (cortisol, corticosterone, aldosterone, androstenedione, testosterone, and dihydrotestosterone) had no effect on spotting.

(B) Dose response: *Hyperolius argus* larvae were treated with 17 β estradiol as in part (A) above, but at doses of 100 ng/ml, 10 ng/ml, 1 ng/ml, and 100 pg/ml. All doses resulted in spotting, but lower doses required longer time periods. Doses of 100 ng/ml and 10 ng/ml induced spotting within four days. The 1 ng/ml dose induced spotting in six days, and the 100 pg/ml dose did not induce spotting until 15 days after treatment was administered. Doses lower than 100 pg/ml were not used due to the lengthy treatment period likely to be required.

(C) Estrogen inhibitors: Tamoxifen was administered at 500 ng/ml, alone and in combination with 17 β estradiol (10 ng/ml) to examine the effects of an estrogen inhibitor (five animals each). The dose of 17 β estradiol used induces spotting within six days when administered alone. Tamoxifen alone did not induce spotting over this time period, and when administered with 17 β estradiol blocked induction of spotting by 17 β estradiol.

(D) Toxins: Diethylstilbestrol (DES, 100 ng/ml), and the ortho,para isomers of DDT, DDE and DDD (1 μg/ml) were dissolved in acetone and administered following the protocol of part (A) above. All exhibited positive spotting activity. The p,p isomers of DDT and its metabolites were all toxic at this concentration, and were not tested further.

Example 2

Androgenic Compounds (A) Testosterone was administered at doses of 10 ng/ml and 100 ng/ml per dose to *Hyperolius argus* (N=90) throughout the larval period. Both dosages induced the male-typical gular pouch development, as evidenced by an extendible pouch and change in skin texture. The lower dosage of testosterone did not induce a fully-developed pouch, and minimal change in skin texture. Normal males do not develop gular pouches until about three months post-metamorphosis. Only androgenic compounds induced gular pouch formation at this age.

(B) Testosterone was administered at doses of 10 ng/ml and 100 ng/ml per dose to *Hyperolius argus* (N=5) six days prior to metamorphic climax. Both dosages induced the male-typical gular pouch development, as evidenced by an extendible pouch and change in skin texture. The lower dosage of testosterone did not induce a fully-developed pouch, and minimal change in skin texture. Normal males do not develop gular pouches until about three months post-metamorphosis. Only androgenic compounds induced gular pouch formation at this age.

Example 3

Thyroid Hormone

Normal *Hyperolius argus* larvae were treated with thiourea (a thyroid hormone antagonist) at 240 µg/ml throughout development. Larvae treated with thiourea completely failed to undergo metamorphosis, but continued to grow.

Example 4

Kits (A) An assay kit is assembled containing the following:
25 *Hyperolius argus* tadpoles;
10 ml estradiol (100 ng/ml);
10 ml testosterone (100 ng/ml);
100 ml thiourea (240 µg/ml); and
100 ml DDT (100 ng/ml).

The kit is provided with instructions for raising the tadpoles, and for administering test compounds or samples to some tadpoles while administering the positive controls (estradiol and testosterone) to others.

(B) Another assay kit of the invention is assembled, containing:
120 *Hyperolius argus* tadpoles;
100 ml estradiol (100 ng/ml);
100 ml testosterone (100 ng/ml).

The kit is provided with instructions for raising the tadpoles, and for administering test compounds or samples to tadpoles while coadministering estradiol or testosterone, to determine compounds having antagonist activity.

What is claimed:

1. A method for assaying hormonal activity, comprising:
    providing hormone-responsive tissue from a larva of a hormone-responsive amphibian species, wherein a male or a female adult derived from said larva of said hormone-responsive amphibian species is identified as a male or a female by a characteristic coloration;
    contacting said tissue with a sample; and
    observing the presence or absence of indicia characteristic of hormonal activity of said amphibian species.

2. The method of claim 1, wherein said amphibian species is *Hyperolius argus*.

3. The method of claim 2, wherein said tissue comprises an intact larva.

4. The method of claim 2, wherein said tissue comprises isolated dorsal skin.

5. The method of claim 2, wherein said tissue comprises isolated ventral skin.

6. The method of claim 2, wherein said tissue comprises an isolated portion of the tail.

7. The method of claim 2, wherein said hormonal activity comprises estrogenic activity.

8. The method of claim 7, wherein said indicia comprises spotting characteristic of female *Hyperolius argus*.

9. The method of claim 8, wherein said indicia comprises the length of time necessary for appearance of spots.

10. The method of claim 2, wherein said hormonal activity comprises androgenic activity.

11. The method of claim 10, wherein said indicia comprises development of a gular pouch.

12. The method of claim 10, wherein said indicia comprises the length of time necessary for appearance of a gular pouch.

13. The method of claim 2, wherein said hormonal activity comprises thyroid hormone activity.

14. The method of claim 13, wherein said indicia comprises tail resorption.

15. The method of claim 13, wherein said indicia comprises the length of time necessary for tail resorption.

16. The method of claim 1, further comprising administering a compound with known positive hormonal activity.

17. The method of claim 2, wherein said hormonal activity comprises estrogenic activity, androgenic activity, and thyroid hormone activity.

18. The method of claim 2, wherein said sample is administered by adding the sample to culture media containing a larva.

19. The method of claim 2, wherein said sample is administered at least about six days prior to the end of metamorphosis.

20. The method of claim 19, wherein said sample is administered substantially throughout metamorphosis.

21. The method of claim 19, wherein said sample is administered substantially throughout the larval stage.

22. A test kit for determining the presence of estrogenic, androgenic, and/or thyroid hormone activity in a sample, said kit comprising:
    *Hyperolius argus* larvae hormone-responsive tissue; and
    a positive control selected from the group consisting of an estrogenic compound, an androgenic compound, and a compound with thyroid hormone activity wherein in the tissue and positive control are in separate media.

23. The kit of claim 22, wherein said tissue comprises an intact larva.

24. The kit of claim 22, wherein said tissue comprises isolated tissue selected from the group consisting of dorsal skin, ventral skin, and a tail portion.

* * * * *

UNITED STATES PATENT AND TRADEMARK OFFICE
CERTIFICATE OF CORRECTION

PATENT NO. : 6,123,918
DATED : September 26, 2000
INVENTOR(S) : Tyrone B. Hayes

It is certified that error appears in the above-identified patent and that said Letters Patent is hereby corrected as shown below:

Table 1, column 4
Lines 28-29, between "17-gluc E2 ++" and "17-SO$_4$ E2 (1µg/ml) +" insert -- 3– SO$_4$ E2 ++ --.

Column 6,
Line 57, delete "in".

Signed and Sealed this

Twenty fifth Day of September, 2001

Attest:

NICHOLAS P. GODICI
Attesting Officer   Acting Director of the United States Patent and Trademark Office